United States Patent [19]

Price et al.

[11] Patent Number: 4,777,143
[45] Date of Patent: Oct. 11, 1988

[54] METHOD OF DETECTING CARBOXYLIC ACIDS IN A SPECIMEN

[75] Inventors: Neil H. Price, San Jose; Paul J. Lawrence, Campbell, both of Calif.

[73] Assignee: Litmus Concepts Inc., Santa Clara, Calif.

[21] Appl. No.: 940,775

[22] Filed: Dec. 12, 1986

[51] Int. Cl.⁴ .................... G01N 33/569; G01N 33/53
[52] U.S. Cl. ...................................... 436/129; 436/76; 436/80; 436/84
[58] Field of Search .................... 436/76, 80, 84, 129, 436/37, 66; 422/61, 78

[56] References Cited

U.S. PATENT DOCUMENTS

| | | | |
|---|---|---|---|
| 2,283,262 | 5/1942 | Kamlet | 436/129 |
| 2,990,253 | 6/1961 | Smeby | 436/129 |
| 3,099,605 | 7/1963 | Free | 436/129 |
| 3,386,806 | 6/1968 | Kross | 436/129 |
| 3,485,588 | 12/1969 | Fouts | 436/129 |
| 3,490,874 | 1/1970 | Ando et al. | 436/129 |
| 3,915,643 | 10/1975 | Gindler | 436/129 |
| 3,980,433 | 9/1976 | Tamura et al. | 436/129 |
| 4,407,962 | 10/1983 | Tabacco et al. | 436/84 |
| 4,486,536 | 12/1984 | Baker et al. | 436/66 |
| 4,615,982 | 10/1986 | Lawrence | 422/56 X |

FOREIGN PATENT DOCUMENTS

| | | | |
|---|---|---|---|
| 121317 | 10/1984 | European Pat. Off. | |
| 49-27075 | 7/1974 | Japan | 436/129 |
| 50-110698 | 8/1975 | Japan | 436/129 |
| 424052 | 9/1974 | U.S.S.R. | 436/129 |
| 640203 | 2/1979 | U.S.S.R. | 436/129 |
| 0828083 | 5/1981 | U.S.S.R. | 436/129 |

OTHER PUBLICATIONS

Ahlquist et al., *Annals of Internal Medicine*, 101: 297-302 (1984).
Alieva et al., *Med. Parazitol. Parazit. Bolez.*, 48(4): 36-39 (1979).
Alieva et al., *Parazitologiya (Leningr)*, 14(1): 71-75 (1980).
Preston and Pankratz, *A Guide to the Analysis of Fatty Acids and Their Esters by Gas Chromatography*, 2nd Ed., Polyscience Corporation (1971, ISBN 0-913106-08-9).
Antonis, *Journal of Lipid Research*, 6: 307-213 (1965).
Itaya and Ui, *Journal of Lipid Research*, 6: 16-20 (1965).
Karnaukhov and Soprunova, *Med. Parazitol. Parazit. Bolez.*, 45(4): 450-452 (1976).
Mangold et al., "Routine Methods of Lipid Analysis—Procedure: Colorimetric Determination of Non-Esterified Fatty Acids . . . ", *Clin. Biochem.—Principles and Methods*, vol. II, p. 1034, Eds. Curtius and Roth, New York: De Gruyther (1978).
Merritt et al., *Am. J. Vet. Res.*, 41(6): 928-931 (1980).
Monteoliva, *Revista Iberica de Parasitologia*, 39:9-17 (1979).
Monteoliva, *Revista Iberica de Parasitologia*, 41:333-340 (1981).
Mosinger, *Journal of Lipid Research*, 6: 157-159 (1965).
Schlierf et al., *Journal of Lipid Research*, 6: 317-319 (1965).
Soprunova, *Angew. Parasitol.*, 14:11-17 (1973).
Soprunov et al., *Acta Tropica*, 38: 449-460 (1981).
Ueno, *J. Biochem.*, 48(2): 161-168 (1960).
Warren and Poole, *Exp. Parasit.*, 24: 408-416 (1970).
Williams and Cokal, *Anal. Chem.*, 58:1541-1547.

*Primary Examiner*—Barry S. Richman
*Assistant Examiner*—Timothy M. McMahon
*Attorney, Agent, or Firm*—Ciotti & Murashige, Irell & Manella

[57] ABSTRACT

A method for detecting the presence of carboxylic acids in a specimen is provided. A specimen is contacted with a developing system containing a metal salt reactive with carboxylic acids present in the specimen to form metal-carboxylic acid complexes. Any such complexes are colorimetrically detected by their activity in catalyzing oxidation of a chromogen such as guaiac. The method is useful in detecting intestinal helminth infestation.

28 Claims, 1 Drawing Sheet

FIG. 1 COMPARISON OF GLUCOSE METABOLISM OF MAMMALS & WORMS

METHOD OF DETECTING CARBOXYLIC ACIDS IN A SPECIMEN

DESCRIPTION

1. Technical Field

This invention relates generally to detection of carboxylic acids in a specimen, and more particularly relates to a catalytic method of detecting free fatty acid (FFA) metabolites produced by intestinal helminths in a host.

2. Background Art

Several investigators have studied the metabolism of intestinal helminths. Soprunov, F. F., et al., in *Acta Tropica* 38: 449–460 (1981), characterized the end products of *Ascaris lumbricoides* metabolism. Y. Ueno, in *J. Biochem.* 48 (2): 161–168 (1960) also studied the metabolism of Ascaris organisms. These studies as well as subsequent work carried out by the inventors herein have demonstrated that intestinal helminths use a highly unusual metabolic pathway which results in the excretion of large quantities of free fatty acids into the host's intestine.

Figure 1:
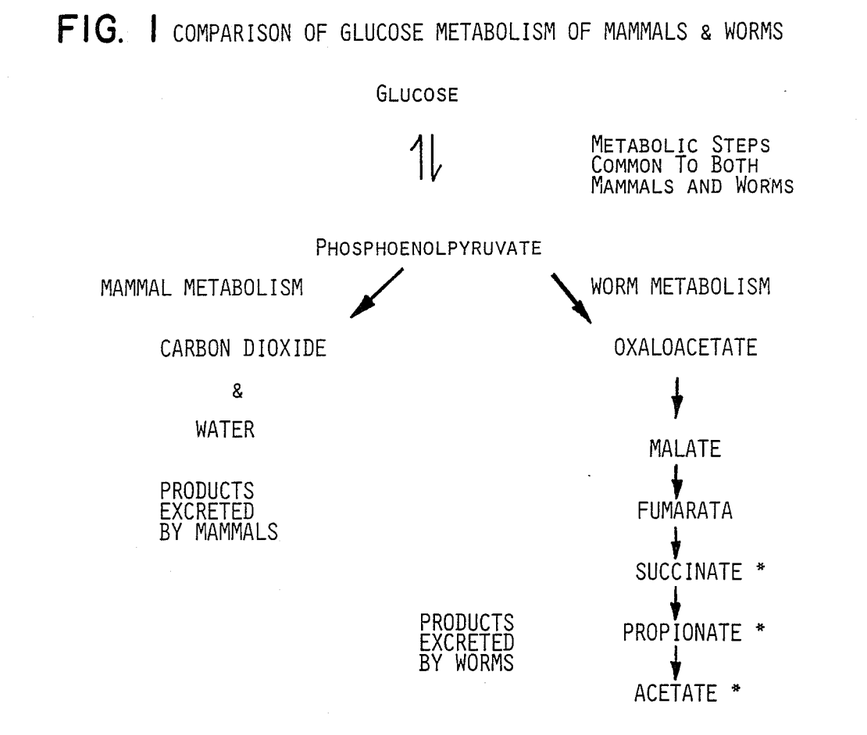
FIG. 1 is a flow chart comparing the glucose metabolism of a vertebrate with that of an intestinal helminth. The helminth metabolites listed may further combine to form longer-chain free fatty acids.

The intestinal parasitic helminths thus differ metabolically from their host in a very significant way. The helminths exist in a largely anaerobic environment and rely almost completely on anaerobic glycolysis as an energy source. The inventors herein have found no evidence that the parasites use lipids or amino acids for energy; helminths and their hosts differ in glycolytic capacity after a key metabolic branch point is reached, as illustrated in FIG. 1. While the host converts phosphoenolpyruvate (PEP) into pyruvate, carbon dioxide and water via the tricarboxylic acid cycle and electron transport chain, helminths are unable to use these last two pathways because of limited oxygen availability. Instead, they excrete large amounts of free fatty acids, including fumaric, succinic, acetic and propionic acids.

In addition to these metabolites, many helminths combine acetic and propionic acids to form FFA products with four, five and six carbon atoms. The resulting carbon chains can be linear or branched, and typically include n-butyric, i-butyric, valeric, 2-methyl butyric, caproic, 2-methyl valeric, 2-methyl caproic, tiglic and 3-methyl butyric acids. Some of these acids are absorbed and metabolized by the host, while some are excreted in the urine and feces. The five- and six-carbon, straight and branched chain free fatty acids are not synthesized by vertebrates and are found in serum, urine, salivary or fecal samples only if helminth infestation is present. It is highly desirable, therefore, to develop a diagnostic test based on excretion of these five- and six-carbon free fatty acids which strongly correlates with helminth infestation.

To date, however, no convenient, simple, on-site test has been developed for detecting helminth infestation based on the presence of these metabolites. Accordingly, the present invention is directed to a method of detecting infestation by the major intestinal helminths, including nematodes such as round, hook and whip worms, and cestodes such as tapeworms, by detecting the corresponding end-product five- and six-carbon FFA metabolites. The present method is also useful in detecting other carboxylic acids.

In a preferred embodiment, the present method is specific for five- and six-carbon FFA metabolites and succinate. The method provides a number of advantages, including (1) specificity for the five- and six-carbon FFA prodcuts as well as for succinate; (2) physical and chemical stability of reagents used; (3) high sensitivity and specificity such that small samples may be used and false positives are substantially eliminated; and (4) detection of FFA at concentrations between about 0.05 and 10 mM, i.e. at concentrations which may be found in serum, fecal, urine and salivary specimens from helminth infested mammals.

DISCLOSURE OF THE INVENTION

One aspect of the invention is a method of detecting carboxylic acids in a specimen, comprising: (a) contacting a specimen with a metal salt reactive with carboxylic acids to form metal-carboxylic acid complexes; and (b) detecting the presence of metal-carboxylic acid complexes which are formed by monitoring the catalytic activity of such complexes.

In another aspect of the invention, the method is used to detect intestinal helminth infestation by detecting the presence of certain intestinal helminth metabolites. The metabolites detected are free fatty acids which are produced by intestinal helminths but not by vertebrates, and which are thus found in serum, fecal, urine and salivary specimens only when infestation is present. These free fatty acids include five- and six-carbon branched and unbranched acids as well as succinic acid. The developing system which contacts the specimen contains an organic solvent selected so that metal-fatty acid complexes formed from these particular acids may be isolated therein and detected independently of any other fatty acids which may be present.

In still another aspect of the invention, a solid phase diagnostic method is provided in which (a) a solid support such as filter paper or the like is provided on which a serum, fecal, urine or salivary sample has been smeared, and (b) the specimen on the support is contacted with a developing system so that, as above, metal-carboxylic acid complexes will form and be detected colorimetrically. A metal salt is present either on the solid support or in an aqueous phase of the developing system.

In still a further aspect of the invention, a developing system for use in detecting carboxylic acids is provided, the system comprising (a) a metal salt reactive with carboxylic acids to form metal-carboxylic acid complexes; (b) an organic phase containing a solvent in which selected metal-carboxylic acid complexes are substantially soluble and in which the metal salt is substantially insoluble; (c) a chromogen; and (d) an oxidant capable of oxidizing the chromogen to a colored compound in the presence of metal-carboxylic acid complexes. The developing system may further include a solid support on which the metal salt is present or an aqueous phase in which the metal salt is substantially dissolved. The chromogen may also be present on the solid support, or it may be dissolved in the organic solvent.

MODES FOR CARRYING OUT THE INVENTION

"Free fatty acids" (FFA) as used herein include the carboxylic acid end products of helminth metabolism, in acid or salt form. Examples of these end products are set forth in Table 1.

TABLE 1

| | Helminthic Metabolite Production | | | |
|---|---|---|---|---|
| | TYPE OF WORM | | | |
| ACID | ROUND | HOOK | WHIP | TAPE |
| Formate | + | | + | |
| Acetate | + | + | + | + |
| Proponate | + | + | + | + |
| n-Butyrate | + | + | + | |
| i-Butyrate | | + | | |
| Valerate | + | | + | + |
| 2-Methyl Butyrate | + | + | | |
| Caproate | | | | |
| 2-Methyl Valerate | + | + | + | |
| 2-Methyl Caproate | + | | | |
| Tiglate | + | | + | |
| 3-Methyl Butyrate | + | + | | |
| Succinate | | | + | + |
| Long Chain FFA | | | | + |
| Lactic Acid | | | + | + |

The subset of these FFA which in a preferred embodiment is detected by the present method includes acids which are produced by helminths but not by vertebrates, so will be present in a specimen only when helminth infestation is present.

"Carboxylic acids" which are detectable by the present method include any carboxylic acids that form metal-acid complexes with the metal salts used herein, the metal-acid complexes so formed being substantially soluble in the selected organic solvent, catalytically active in the present method, and preferably mobile on a solid support. The carboxylic acids also (1) are substantially soluble in aqueous solution, (2) are of a structure such that steric considerations are not problematic in metal-acid complex formation, (3) are not substantially reactive with other components of the developing system, and (4) are relatively chemically and physically stable for a period of time at least sufficient to be detected by the present method.

A "developing system" is one which will react with a specimen so as to produce a positive test when carboxylic acids are present and a negative test otherwise. The positive test is typically a color change that is visible to the naked eye.

A "chromogen" is a compound which is capable of producing a colored substance under certain conditions. Normally, the compound is colorless in a reduced state, and upon oxidation with a suitable oxidant, becomes colored in the oxidized state.

"Substantially soluble" metal-carboxylic acid complexes are those acids which, at concentrations typically found in serum, fecal, urine or salivary specimens, are soluble in a solvent to an extent that they are detectable by the method presented herein. Metal salts which are "substantially insoluble" in an organic solvent are insufficiently extracted into the organic phase to be colorimetrically detected therein.

A "substantially water-immiscible" organic solvent is one which will sufficiently phase separate from an aqueous layer so that extraction of metal-carboxylic acid complexes into an organic phase from an aqueous layer is possible.

"Catalytically active" metal salts and metal-carboxylic acid complexes are capable of oxidizing a chromogen in the presence of an oxidant. For example, in a preferred embodiment of the present invention, the metal salts and complexes formed therefrom catalyze the oxidation of guaiac in the presence of cumene hydroperoxide. Typically, catalytically active metal-carboxylic acid complexes are formed from catalytically active metal salts.

In the present method, a specimen to be analyzed is initially contacted with a metal salt reactive with carboxylic acids in the specimen to form metal-carboxylic acid complexes which catalyze a colorimetric reaction. These complexes are thus detected by monitoring of their catalytic activity. In a preferred embodiment, the complexes are detected by their activity in catalyzing oxidation of a chromogen by an oxidant to a colored state.

The metal salt is preferably a catalytically active compound selected from the group consisting of iron, silver and copper salts. Particularly preferred metal salts for use herein are iron, silver and copper chlorides, sulfates and nitrates, although organic salts (e.g., acetate, propionate) of these metals may be used as well. In the latter case, the organic salts should not, clearly, be formed from any of the carboxylic acids to be detected, nor should they interfere with the detection in any other way. The organic salts should not be reactive with any of the components of the developing system, nor should they present steric, solubility or stability problems.

The metal salt is initially present in the developing system. In one embodiment, the developing system contains an aqueous phase in which the metal salt is substantially dissolved; in an alternative embodiment, the developing system contains a solid support on which the metal salt is provided. In the former case, preferred concentrations of metal salt in solution range from about 0.5 to about 50 mM; particularly preferred concentrations range from about 1.0 to about 10 mM. In the latter case, i.e. where the solid support is pre-treated with a metal salt, the water contained in the specimen is sufficient to form a suitable aqueous phase.

The solvent is chosen so as to selectively dissolve certain metal-carboxylic acid complexes and not others. In general, suitable solvents include organic solvents (1) in which metal-carboxylic acid complexes formed from selected carboxylic acids are substantially soluble, (2) in which the metal salt is substantially insoluble, (3) are water immiscible, and (4) substantially dissolve other reagents present, including the chromogen and oxidant.

The free fatty acids typically produced by intestinal helminths are set forth in Table 1. It should be noted that by varying the solvent selected for use in the developing system, entirely different groups of free fatty acids may be detected. As may be seen in Table 1, certain patterns of FFA produced can correspond to infestation by different intestinal helminths; the method herein may thus be used to distinguish between these helminths.

In a preferred embodiment of the invention, five- and six-carbon free fatty acid helminth metabolites are detected including valeric, caproic, tiglic, and 2- and 3-methyl butyric acids. Succinic acid is detected as well. For this preferred application, suitable solvents include toluene, halogenated hydrocarbons such as 1,1,1-trichloroethane, benzyl alcohol, isopropyl benzyl alcohol, dichloromethane, ethyl acetate, octyl acetate, cumene, benzyl benzoate, alcohols having from about six to about eleven carbon atoms (e.g., hexanol), and mixtures thereof. Alcohols with twelve or more carbon atoms are typically solids at room temperature and are thus excluded from use in the present method.

The diagnostic method also involves contacting the specimen with a chromogen and an oxidant capable of oxidizing the chromogen. In a preferred embodiment, both the chromogen and the oxidant are present in the organic phase of the developing solution.

Any metal-carboxylic acid complexes present in the solvent catalyze the oxidation of the chromogen by the oxidant. Chromogens are selected so that a definite color change is visible to the naked eye upon oxidation. Suitable chromogens are selected from the group consisting of guaiac, 4-chloro-1-naphthol, ortho-phenylenediamine, tetramethylbenzidine, leucomalachite green, 2,2-azinobis (3-methoxy diphenylamine), ortho-dianisidine, 5-amino salicylic acid, and mixtures thereof. A particularly preferred chromogen is guaiac, which is colorless in its reduced state and deep blue in its oxidized state. Optionally, the chromogen may be purified prior to use, e.g. by solvent extraction.

Preferred concentrations of chromogen in solution vary with the solvent system selected. Typically, chromogen concentration will range from about 0.01 wt.% to about 2.0 wt.%. Lower concentrations in this range are appropriate for a hexanol system, while higher concentrations are preferable for trichloroethane systems or for a toluene/hexane mixture.

Suitable oxidants include hydrogen peroxide or organic hydroperoxides such as cumene hydroperoxide, t-butyl hydroperoxide, diisopropylbenzene hydroperoxide, 2,5-dimethylhexane hydroperoxide and mixtures thereof. Organic hydroperoxides are preferred, and a particularly preferred oxidant is cumene hydroperoxide.

The concentration of oxidant, again, will vary with the particular solvent system chosen. Typically, oxidant concentration will range from about 0.02 wt.% to about 1.0 wt.%, the lower concentrations in this range corresponding to hexanol systems or to a toluene/hexanol mixture, and the higher concentrations corresponding to a pure toluene or trichloroethane system.

The specimen to be analyzed for carboxylic acids is provided on a solid support, and optionally acidified prior to development. The specimen is then contacted with the developing system for a time sufficient to allow full color development, i.e. to allow observation of any color change due to the presence of metal-carboxylic acid complexes. Generally, the colored product will be noticeable in less than about one minute, although longer incubation times are sometimes employed so as to ensure detection of lower carboxylic acid concentrations. Incubation times are preferably shorter than about 1 minute, but may, if desired, be extended for 15 minutes or more to ensure detection of low concentrations of carboxylic acids. Shorter development times are preferred.

The pH of the developing system may vary, although neither a very low pH nor a very high pH is desirable. The method herein is effective in a pH range of about 4 to about 11, and a preferred pH is about 7. Optionally, the developing system may be buffered to a particular pH, e.g. 7, with suitable buffering agents.

The sensitivity of the present method is substantially higher than that which is the minimum necessary to detect helminth infestation. As demonstrated in the Examples, free fatty acid concentrations as low as 0.05 mM can be detected with the method, while the ability to detect concentrations on the order of 1 to 10 mM can be sufficient to detect infestation.

The metal salt, chromogen and oxidant may all be present on a solid support. In alternative embodiments, one or more of these reagents may be present in solution, the metal salt in aqueous solution and the chromogen or oxidant or both present in the organic solvent.

In a second aspect of the invention, a solid phase diagnostic method is provided in which (a) a solid support such as a filter paper or the like is provided on which a serum, fecal, urine or salivary sample has been smeared or spotted, and (b) the specimen on the support is contacted with a developing system so that, as above, metal-carboxylic acid complexes will form and be detected colorimetrically. The reagents necessary to effect this diagnostic method are as above, i.e. a developing system which includes a metal salt reactive with carboxylic acids, which salt may be present either on the solid support or in an aqueous phase, a chromogen, an oxidant, and an organic solvent in which selected metal-carboxylic acid complexes are substantially soluble and in which the metal salt is substantially insoluble. One or both of the chromogen and oxidant may be present on the solid support, or in the organic solvent.

In another aspect of the invention, a developing system is provided which is useful in detecting carboxylic acids, e.g. the free fatty acid metabolites produced in intestinal helminth infestation. The developing system comprises a metal salt reactive with carboxylic acids to form metal-carboxylic acid complexes, an organic phase containing a solvent in which selected metal-fatty acid complexes are substantially soluble and in which the metal salt is substantially insoluble, a chromogen, and an oxidant capable of oxidizing the chromogen. The developing system may further include a solid support on which the metal salt is provided, or an aqueous phase in which the metal salt is substantially dissolved. One or both of the chromogen and oxidant may be present on a solid support, or in the organic solvent. In a preferred embodiment, the metal salt is a copper salt, the chromogen is guaiac and the oxidant is cumene hydroperoxide.

While the invention has been described in conjunction with the specific embodiments thereof, the foregoing description as well as the examples which follow are intended to illustrate and not limit the scope of the invention, which is defined by the appended claims. Other aspects, advantages and modifications not explicitly addressed herein but apparent to one skilled in the art to which the invention pertains are considered within the scope of the invention as well.

Experimental: All chemicals used herein are commercially available from Sigma Chemical Co., Aldrich Chemical Co., J. T. Baker Co., Mallinckrodt and Lancaster Synthesis, Ltd.

EXAMPLE 1

Utility of Solvents for Detecting Free Fatty Acids

Various solvents were tested for their utility with regard to (1) water miscibility, (2) guaiac solubility and (3) color development. Water miscibility was evaluated by admixing 0.5 ml of water with 0.5 ml each solvent, and noting any phase separation. Where phase separation was visible, a "−" appears in Table 2; otherwise, a "+" appears.

Color developing reagent was prepared as follows. 0.200 ml of 0.375 wt.% guaiac solution in ethanol were added to individual clean test tubes and the ethanol evaporated. Four ml of a given solvent as indicated in Table 2 were added and the guaiac was allowed to dissolve to the extent possible. Solubility of guaiac in each solvent was noted visually and is set forth in Table 2. Solvents which dissolved essentially all of the deposited guaiac produced a distinct yellow-brown color (+++); those which dissolved an intermediate amount of guaiac produced a medium yellow color (++); and those which dissolved only a small amount of the guaiac produced a light yellow color (+). Solvents which dissolved essentially none of the guaiac remained colorless (−).

Subsequently, 48 μl of 80% cumene hydroperoxide was added to each tube (except to that containing the water-only sample) to make a complete color developing reagent (solvent, chromogen, oxidant) for testing. Since cumene hydroperoxide is essentially insoluble in water, hydrogen peroxide was used as the oxidant in the water-only sample instead. However, the guaiac was insufficiently soluble in water to provide adequate color development.

Tests evaluating color development were conducted by adding 50 μl of test sample, 30 μl 1 mM cupric sulfate and 100 μl color developing reagent to microtiter plate wells. Fatty acid test samples were 100 mM in distilled water and titrated with dilute sodium hydroxide to produce a final pH of 7.0. Color intensity was scored as follows: 0=no blue color perceptible; 1=barely perceptible production of blue color; 2=faintest blue color clearly and reliably detectable; 3-9=intermediate color change; and 10=maximum color production. Results are set forth in Table 2.

TABLE 2

| SOLVENT | WATER MISCIBILITY | GUAIAC SOLUBILITY | COLOR INTENSITY SCORE AT 5 MINUTES ||||||||
|---|---|---|---|---|---|---|---|---|---|---|
| | | | H$_2$O | NaCl | Me—C-4 | C-5 | Me—C-5 | SUC. | LAC. | CIT |
| Water | | − | 0 | 0 | 0 | 0 | 0 | 0 | 0 | 0 |
| Methanol | + | +++ | 10 | 10 | 10 | 10 | 10 | 10 | 10 | 0 |
| Ethanol | + | +++ | 10 | 10 | 10 | 10 | 10 | 10 | 10 | 0 |
| Isopropanol | + | +++ | 10 | 10 | 10 | 10 | 10 | 10 | 10 | 0 |
| n-Butanol | − | +++ | 2 | 10 | 10 | 10 | 10 | 10 | 10 | 0 |
| n-Pentanol | − | +++ | 2 | 4 | 10 | 10 | 10 | 5 | 2 | 0 |
| n-Hexanol | − | +++ | 0 | 3 | 9 | 7 | 8 | 2 | 1 | 0 |
| n-Heptanol | − | +++ | 0 | 0 | 10 | 7 | 7 | 2 | 1 | 0 |
| n-Octanol | − | +++ | 0 | 0 | 3 | 3 | 3 | 2 | 1 | 0 |
| Ethylene Glycol | + | +++ | 8 | 8 | 8 | 7 | 8 | 7 | 7 | 2 |
| Benzyl Alcohol | − | +++ | 3 | 6 | 10 | 10 | 8 | 2 | 1 | 0 |
| 4-Isopropyl-Benzyl Alcohol | − | +++ | 3 | 6 | 10 | 10 | 8 | 2 | 1 | 0 |
| Acetone | + | +++ | 10 | 10 | 10 | 10 | 10 | 10 | 10 | 0 |
| 4-hydroxy, 4 methyl-pentanone | + | +++ | 10 | 10 | 10 | 10 | 10 | 10 | 10 | 0 |
| Methyl Ethyl Ketone | + | +++ | 1 | 7 | 10 | 10 | 10 | 9 | 2 | 1 |
| Ethyl Acetate | − | ++ | 1 | 2 | 8 | 9 | 8 | 7 | 1 | 0 |
| Methyl-Acetoacetate | + | +++ | 0 | 5 | 0 | 0 | 0 | 0 | 0 | 0 |
| Octyl Acetate | − | ++ | 1 | 2 | 8 | 8 | 8 | 3 | 2 | 1 |
| Benzyl Benzoate | − | ++ | 0 | 0 | 6 | 3 | 6 | 0 | 0 | 0 |
| Hexanes | − | − | 0 | 1 | 2 | 2 | 2 | 2 | 0 | 0 |
| n-Octane | − | − | 0 | 1 | 0 | 1 | 1 | 0 | 0 | 0 |
| Cumene | − | + | 0 | 0 | 5 | 5 | 5 | 1 | 1 | 0 |
| Toluene | − | + | 0 | 0 | 6 | 6 | 6 | 2 | 2 | 0 |
| Dichloromethane | − | ++ | 6 | 8 | 10 | 10 | 10 | 10 | 10 | 6 |
| Chloroform | − | +++ | 3 | 3 | 6 | 7 | 6 | 4 | 4 | 0 |
| 1,1,1-trichloroethane | − | ++ | 4 | 1 | 8 | 9 | 9 | 5 | 4 | 0 |

EXAMPLE 2

Solvent Extraction of FFA-Copper Salts

Based on the initial screening of Example 1, four solvent systems were selected for further testing: toluene, 1,1,1-trichloroethane ("TCE"), n-hexanol and a 90:10 v/v toluene/hexanol solvent mixture. These solvents were tested for their ability to selectively extract copper ion-fatty acid complexes formed from FFA of varying chain length. 100 μl copper sulfate solution (800 mM) and 100 μl fatty acid solution (100 mM, titrated with sodium hydroxide to a pH of 7 or 100 μl sodium chloride (100 mM) were added to a clean test tube. 500 μl of solvent were added, and the reagent mixture was vortexed for 30 seconds. The phases were allowed to separate, and 100 μl of the organic phase were added to 100 μl of color developing agent containing 1 wt.% cumene hydroperoxide and 0.55 wt.% guaiac in hexanol. Color development was monitored as in Example 1, and results are set forth in Table 3.

TABLE 3

| | LENGTH OF FATTY ACID CARBON CHAIN |||||||||||||||
|---|---|---|---|---|---|---|---|---|---|---|---|---|---|---|---|
| SOLVENT | NaCl | C1 | C2 | C3 | iC4 | C5 | Me—C4 | C6 | Me—C5 | Me—C6 | C8 | C10 | C12 | C16 | Succinate |
| | RESULTS WITH GUAIAC DETECTION SYSTEM |||||||||||||||
| Toluene | 0 | 0 | 0 | 0 | 0 | 2 | 3 | 10 | 9 | 10 | 10 | 10 | 10 | 4 | 0 |
| Hexanol | 1 | 3 | 2 | 3 | 4 | 6 | 3 | 4 | 3 | 4 | 3 | 5 | 7 | 0 | 2 |
| TCE | 0 | 0 | 0 | 0 | 0 | 7 | 9 | 10 | 10 | 10 | 10 | 10 | 10 | 4 | 0 |

TABLE 3-continued

| SOLVENT | LENGTH OF FATTY ACID CARBON CHAIN | | | | | | | | | | | | | | |
|---|---|---|---|---|---|---|---|---|---|---|---|---|---|---|---|
| | NaCl | C1 | C2 | C3 | iC4 | C5 | Me—C4 | C6 | Me—C5 | Me—C6 | C8 | C10 | C12 | C16 | Succinate |
| TOL/HEX | 0 | 0 | 0 | 0 | 1 | 5 | 3 | 5 | 7 | 8 | 4 | 6 | 9 | 9 | 0 |

Hexanol extracted all of the FFA tested between a chain length of 1 and 12. Toluene and TCE produced a strong color only with FFA having a chain length of 5-6 carbon atoms. The toluene/hexanol mixture extracted all of the FFA having a chain length between 5 and 16. Thus, the data in Table 3 indicate that it is possible to selectively extract FFA by varying the solvent.

EXAMPLE 3

Performance of Alternative Metal Ions

Various metal ions were tested for their ability to catalyze the oxidation of guaiac by cumene hydroperoxide. Metal salts were provided in aqueous solutions having concentrations of 0.001M and 1.0M. These solutions were admixed with 20 μl 100 mM butyric acid, titrated with sodium hydroxide to a pH of 7.0, and 100 μl of a color developing reagent containing 0.5 wt.% guaiac and 5 wt.% cumene hydroperoxide in hexanol, and color formation was monitored as in the previous examples. Results are set forth in Table 4.

TABLE 4

| | | COLOR SCORES AT 1-2 MINUTES | |
|---|---|---|---|
| | | METAL CONCENTRATION | |
| METAL | TEST SAMPLE | .001 M | 1.0 M |
| PbNO3 | BLANK | 0 | 0 |
| | TEST | 0 | 0 |
| MnCl2 | BLANK | 0 | 0 |
| | TEST | 0 | 0 |
| CaCl2 | BLANK | 0 | 0 |
| | TEST | 0 | 0 |
| CrCl3 | BLANK | 0 | 0 |
| | TEST | 0 | 0 |
| NiCl2 | BLANK | 0 | 0 |
| | TEST | 0 | 0 |
| AlCl3 | BLANK | 0 | 0 |
| | TEST | 0 | 0 |
| AgNO3 | BLANK | 0 | 0 |
| | TEST | 0 | 9 |
| FeCl3 | BLANK | 0 | 9 |
| | TEST | 0 | 9 |
| CuSO4 | BLANK | 0 | 8 |
| | TEST | 8 | 10 |
| ZnCl2 | BLANK | 0 | 0 |
| | TEST | 0 | 0 |

As may be seen, only silver, copper and iron salts were found to be suitable catalysts at the concentrations tested.

Substrate specificity of these salts was then evaluated with butyric and succinic acid solutions. 20 μl of a metal salt solution (0.001M CuSO4 or 1.0M AgNO3) and 100 μl of 100 mM butyric or succinic acids (titrated with sodium hydroxide to a pH of 7) were added to a clean test tubes. 100 μl of a color developing reagent containing 0.5 wt.% guaiac and 1 wt.% cumene hydroperoxide in hexanol were added, and color formation was monitored after 5 minutes of incubation.

TABLE 5

| | COLOR INTENSITY AT 5 MINUTES | |
|---|---|---|
| | TEST IONS | |
| TEST SOLUTION | .001 M CuSO4 | 1.0 M AgNO3 |
| 0.1 M Butyrate | 10 | 8 |
| 0.1 M Succinate | 8 | 0 |

The results summarized in Table 5 illustrate that the choice of metal salt may be useful in differential diagnosis, i.e. where different color intensities are produced upon reaction of a metal salt (here, AgNO3) with different free fatty acids.

EXAMPLE 4

Component Concentration: Chromogen, Oxidant and Metal Salt

Suitable concentration ranges for chromogen and oxidant were determined for two time intervals: (1) a two-minute incubation time; and (2) a ten-minute incubation time. The chromogen in each of these tests was guaiac, at concentrations varying from 0.001 wt.% to 2.0 wt.% as shown in Tables 6a-6h. The oxidant was cumene hydroperoxide, also at varying concentrations as indicated. Optimum concentration ranges were evaluated according to the following protocol. 100 μl 2.0 mM n-caproic acid (or water in the case of blanks), titrated with sodium hydroxide to a pH of 7.0, 60 μl 1.0 mM cupric sulfate and 100 μl color developing reagent containing guaiac and cumene hydroperoxide at concentrations indicated were added to a clean test tube and vortexed for 10 seconds. Color change was monitored as in the previous Examples. Results are tabulated in Tables 6a through 6h.

TABLE 6a

| SOLVENT = HEXANOL | | | | | | | |
|---|---|---|---|---|---|---|---|
| | | COLOR INTENSITY AT 2 MINUTES | | | | | |
| | | CUMENE HYDROPEROXIDE CONCENTRATION (%) | | | | | |
| SAMPLE TYPE | GUAIAC CONC. (%) | 1.0 | 0.4 | 0.2 | 0.02 | 0.002 | 0.0002 |
| BLANK | 2.0 | 0 | 0 | 0 | 0 | 0 | 0 |
| TEST | | 10 | 9 | 8 | 7 | 6 | 6 |
| BLANK | 1.0 | 0 | 0 | 0 | 0 | 0 | 0 |
| TEST | | 10 | 10 | 8 | 7 | 4 | 4 |
| BLANK | 0.5 | 0 | 0 | 0 | 0 | 0 | 0 |
| TEST | | 10 | 10 | 9 | 7 | 3 | 2 |
| BLANK | 0.10 | 1 | 1 | 1 | 1 | 0 | 0 |
| TEST | | 8 | 8 | 7 | 6 | 2 | 2 |
| BLANK | 0.01 | 0 | 0 | 0 | 0 | 0 | 0 |
| TEST | | 5 | 5 | 5 | 4 | 2 | 0 |
| BLANK | 0.001 | 0 | 0 | 0 | 0 | 0 | 0 |
| TEST | | 3 | 3 | 3 | 3 | 2 | 1 |

TABLE 6b

SOLVENT = TOLUENE

| SAMPLE TYPE | GUAIAC CONC. (%) | COLOR INTENSITY AT 2 MINUTES CUMENE HYDROPEROXIDE CONCENTRATION (%) | | | | | |
|---|---|---|---|---|---|---|---|
| | | 1.0 | 0.4 | 0.2 | 0.02 | 0.002 | 0.0002 |
| BLANK | 2.0 | 0 | 0 | 0 | 0 | 0 | 0 |
| TEST | | 3 | 3 | 2 | 1 | 1 | 1 |
| BLANK | 1.0 | 0 | 0 | 0 | 0 | 0 | 0 |
| TEST | | 2 | 1 | 1 | 1 | 0 | 0 |
| BLANK | 0.5 | 0 | 0 | 0 | 0 | 0 | 0 |
| TEST | | 2 | 2 | 1 | 0 | 0 | 0 |
| BLANK | 0.10 | 0 | 0 | 0 | 0 | 0 | 0 |
| TEST | | 0 | 0 | 0 | 0 | 0 | 0 |
| BLANK | 0.01 | 0 | 0 | 0 | 0 | 0 | 0 |
| TEST | | 0 | 0 | 0 | 0 | 0 | 0 |
| BLANK | 0.001 | 0 | 0 | 0 | 0 | 0 | 0 |
| TEST | | 0 | 0 | 0 | 0 | 0 | 0 |

TABLE 6c

SOLVENT = 90% TOLUENE 10% HEXANOL

| SAMPLE TYPE | GUAIAC CONC. (%) | COLOR INTENSITY AT 2 MINUTES CUMENE HYDROPEROXIDE CONCENTRATION (%) | | | | | |
|---|---|---|---|---|---|---|---|
| | | 1.0 | 0.4 | 0.2 | 0.02 | 0.002 | 0.0002 |
| BLANK | 2.0 | 0 | 0 | 0 | 0 | 0 | 0 |
| TEST | | 9 | 8 | 7 | 6 | 3 | 2 |
| BLANK | 1.0 | 0 | 0 | 0 | 0 | 0 | 0 |
| TEST | | 10 | 10 | 8 | 6 | 2 | 2 |
| BLANK | 0.5 | 0 | 0 | 0 | 0 | 0 | 0 |
| TEST | | 10 | 9 | 8 | 6 | 2 | 1 |
| BLANK | 0.10 | 1 | 1 | 1 | 0 | 0 | 0 |
| TEST | | 7 | 6 | 5 | 3 | 1 | 1 |
| BLANK | 0.01 | 0 | 0 | 0 | 0 | 0 | 0 |
| TEST | | 3 | 3 | 3 | 2 | 1 | 0 |
| BLANK | 0.001 | 0 | 0 | 0 | 0 | 0 | 0 |
| TEST | | 1 | 1 | 1 | 1 | 0 | 0 |

TABLE 6d

SOLVENT = 1,1,1-TRICHLOROETHANE

| SAMPLE TYPE | GUAIAC CONC. (%) | COLOR INTENSITY AT 2 MINUTES CUMENE HYDROPEROXIDE CONCENTRATION (%) | | | | | |
|---|---|---|---|---|---|---|---|
| | | 1.0 | 0.4 | 0.2 | 0.02 | 0.002 | 0.0002 |
| BLANK | 2.0 | 0 | 0 | 0 | 0 | 0 | 0 |
| TEST | | 10 | 4 | 4 | 1 | 1 | 1 |
| BLANK | 1.0 | 0 | 0 | 0 | 0 | 0 | 0 |
| TEST | | 10 | 6 | 4 | 1 | 1 | 1 |
| BLANK | 0.5 | 0 | 0 | 0 | 0 | 0 | 0 |
| TEST | | 10 | 8 | 6 | 2 | 1 | 1 |
| BLANK | 0.10 | 0 | 0 | 0 | 0 | 0 | 0 |
| TEST | | 8 | 6 | 5 | 3 | 0 | 0 |
| BLANK | 0.01 | 0 | 0 | 0 | 0 | 0 | 0 |
| TEST | | 1 | 2 | 3 | 2 | 1 | 0 |
| BLANK | 0.001 | 0 | 0 | 0 | 0 | 0 | 0 |
| TEST | | 0 | 0 | 0 | 0 | 0 | 0 |

TABLE 6e

SOLVENT = HEXANOL

| SAMPLE TYPE | GUAIAC CONC. (%) | COLOR INTENSITY AT 10 MINUTES CUMENE HYDROPEROXIDE CONCENTRATION (%) | | | | | |
|---|---|---|---|---|---|---|---|
| | | 1.0 | 0.4 | 0.2 | 0.02 | 0.002 | 0.0002 |
| BLANK | 2.0 | 1 | 1 | 1 | 0 | 0 | 0 |
| TEST | | 10 | 10 | 10 | 9 | 8 | 6 |
| BLANK | 1.0 | 1 | 1 | 1 | 0 | 0 | 0 |
| TEST | | 10 | 10 | 10 | 9 | 7 | 6 |
| BLANK | 0.5 | 4 | 3 | 0 | 0 | 0 | 0 |
| TEST | | 10 | 10 | 10 | 8 | 6 | 5 |
| BLANK | 0.10 | 1 | 1 | 0 | 0 | 0 | 0 |
| TEST | | 8 | 8 | 8 | 6 | 3 | 2 |
| BLANK | 0.01 | 0 | 0 | 0 | 0 | 0 | 0 |
| TEST | | 5 | 5 | 5 | 5 | 2 | 1 |
| BLANK | 0.001 | 0 | 0 | 0 | 0 | 0 | 0 |
| TEST | | 3 | 3 | 3 | 3 | 2 | 1 |

TABLE 6f

SOLVENT = TOLUENE

| SAMPLE TYPE | GUAIAC CONC. (%) | COLOR INTENSITY AT 10 MINUTES CUMENE HYDROPEROXIDE CONCENTRATION (%) | | | | | |
|---|---|---|---|---|---|---|---|
| | | 1.0 | 0.4 | 0.2 | 0.02 | 0.002 | 0.0002 |
| BLANK | 2.0 | 0 | 0 | 0 | 0 | 0 | 0 |
| TEST | | 5 | 5 | 2 | 1 | 1 | 1 |
| BLANK | 1.0 | 0 | 0 | 0 | 0 | 0 | 0 |
| TEST | | 3 | 2 | 2 | 1 | 0 | 0 |
| BLANK | 0.5 | 0 | 0 | 0 | 0 | 0 | 0 |
| TEST | | 3 | 2 | 1 | 0 | 0 | 0 |
| BLANK | 0.10 | 0 | 0 | 0 | 0 | 0 | 0 |
| TEST | | 1 | 1 | 1 | 0 | 0 | 0 |
| BLANK | 0.01 | 0 | 0 | 0 | 0 | 0 | 0 |
| TEST | | 0 | 0 | 0 | 0 | 0 | 0 |
| BLANK | 0.001 | 0 | 0 | 0 | 0 | 0 | 0 |
| TEST | | 0 | 0 | 0 | 0 | 0 | 0 |

TABLE 6g

SOLVENT = 90% TOLUENE 10% HEXANOL

| SAMPLE TYPE | GUAIAC CONC. (%) | COLOR INTENSITY AT 10 MINUTES CUMENE HYDROPEROXIDE CONCENTRATION (%) | | | | | |
|---|---|---|---|---|---|---|---|
| | | 1.0 | 0.4 | 0.2 | 0.02 | 0.002 | 0.0002 |
| BLANK | 2.0 | 0 | 0 | 0 | 0 | 0 | 0 |
| TEST | | 9 | 9 | 8 | 6 | 3 | 2 |
| BLANK | 1.0 | 0 | 0 | 0 | 0 | 0 | 0 |
| TEST | | 10 | 10 | 8 | 6 | 2 | 2 |
| BLANK | 0.5 | 0 | 0 | 0 | 0 | 0 | 0 |
| TEST | | 10 | 10 | 10 | 7 | 2 | 2 |
| BLANK | 0.10 | 3 | 3 | 2 | 1 | 0 | 0 |
| TEST | | 7 | 7 | 6 | 4 | 2 | 1 |
| BLANK | 0.01 | 0 | 0 | 0 | 0 | 0 | 0 |
| TEST | | 3 | 3 | 3 | 2 | 1 | 0 |
| BLANK | 0.001 | 0 | 0 | 0 | 0 | 0 | 0 |
| TEST | | 0 | 0 | 1 | 1 | 1 | 0 |

TABLE 6h

SOLVENT = 1,1,1-TRICHLOROETHANE

| SAMPLE TYPE | GUAIAC CONC. (%) | COLOR INTENSITY AT 10 MINUTES CUMENE HYDROPEROXIDE CONCENTRATION (%) | | | | | |
|---|---|---|---|---|---|---|---|
| | | 1.0 | 0.4 | 0.2 | 0.02 | 0.002 | 0.0002 |
| BLANK | 2.0 | 3 | 0 | 0 | 0 | 0 | 0 |
| TEST | | 10 | 5 | 6 | 2 | 1 | 1 |
| BLANK | 1.0 | 0 | 0 | 0 | 0 | 0 | 0 |
| TEST | | 10 | 6 | 5 | 2 | 1 | 1 |
| BLANK | 0.5 | 1 | 0 | 0 | 0 | 0 | 0 |
| TEST | | 10 | 8 | 6 | 3 | 2 | 2 |
| BLANK | 0.10 | 0 | 0 | 0 | 0 | 0 | 0 |
| TEST | | 7 | 7 | 5 | 4 | 2 | 1 |
| BLANK | 0.01 | 0 | 0 | 0 | 0 | 0 | 0 |
| TEST | | 0 | 1 | 1 | 1 | 1 | 0 |
| BLANK | 0.001 | 0 | 0 | 0 | 0 | 0 | 0 |

TABLE 6h-continued

SOLVENT = 1,1,1-TRICHLOROETHANE

| SAMPLE TYPE | GUAIAC CONC. (%) | COLOR INTENSITY AT 10 MINUTES CUMENE HYDROPEROXIDE CONCENTRATION (%) | | | | | |
|---|---|---|---|---|---|---|---|
| | | 1.0 | 0.4 | 0.2 | 0.02 | 0.002 | 0.0002 |
| TEST | | 0 | 0 | 0 | 0 | 0 | 0 | with sodium hydroxide to a pH of 7.0, 60 μl cupric sulfate at varying concentrations as indicated in Tables 7a–7d, and 200 μl color developing reagent containing guaic and cumene hydroperoxide were added to a clean test tube. The mixture was vortexed for 10 seconds. Color change was monitored as in the previous examples, after incubation times of 2 and 15 minutes. Results are summarized in Tables 7a through 7d.

TABLE 7a

SOLVENT = TOLUENE
COLOR INTENSITY AT 2 MINUTES AND 15 MINUTES
COPPER CONCENTRATION (millimolar)

| Guaiac (%) | CHP (%) | Sample Type | .5 | | 1.0 | | 2.0 | | 5.0 | | 10 | | 20 | | 50 | |
|---|---|---|---|---|---|---|---|---|---|---|---|---|---|---|---|---|
| | | | 2 M | 15 M | 2 M | 15 M | 2 M | 15 M | 2 M | 15 M | 2 M | 15 M | 2 M | 15 M | 2 M | 15 M |
| 2.0 | 1.0 | BLANK | 0 | 0 | 0 | 0 | 0 | 0 | 0 | 0 | 0 | 1 | 1 | 4 | 1 | 4 |
| | | TEST | 1 | 4 | 5 | 8 | 6 | 8 | 7 | 10 | 7 | 10 | 7 | 10 | 7 | 10 |
| 0.5 | 1.0 | BLANK | 0 | 1 | 0 | 1 | — | — | 0 | 1 | 0 | 1 | — | — | 0 | 1 |
| | | TEST | 0 | 2 | 2 | 4 | — | — | 4 | 5 | 5 | 5 | — | — | 4 | 5 |
| 2.0 | 1.0 | BLANK | 0 | 0 | 0 | 0 | — | — | 0 | 0 | 0 | 0 | — | — | 0 | 0 |
| | | TEST | 0 | 2 | 0 | 0 | — | — | 5 | 7 | 5 | 7 | — | — | 6 | 7 |

TABLE 7b

SOLVENT = HEXANOL
COLOR INTENSITY AT 2 MINUTES AND 15 MINUTES
COPPER CONCENTRATION (millimolar)

| Guaiac (%) | CHP (%) | Sample Type | .5 | | 1.0 | | 2.0 | | 5.0 | | 10 | | 20 | | 50 | |
|---|---|---|---|---|---|---|---|---|---|---|---|---|---|---|---|---|
| | | | 2 M | 15 M | 2 M | 15 M | 2 M | 15 M | 2 M | 15 M | 2 M | 15 M | 2 M | 15 M | 2 M | 15 M |
| 2.0 | 1.0 | BLANK | 0 | 0 | 0 | 0 | 0 | 0 | 0 | 7 | 1 | 8 | 2 | 10 | 2 | 10 |
| | | TEST | 0 | 4 | 10 | 10 | 10 | 10 | 10 | 10 | 10 | 10 | 10 | 10 | 10 | 10 |
| 0.5 | 1.0 | BLANK | 0 | 0 | 1 | 4 | — | — | 4 | 7 | 5 | 7 | — | — | 5 | 8 |
| | | TEST | 5 | 7 | 8 | 8 | — | — | 8 | 8 | 8 | 8 | — | — | 8 | 8 |
| 0.1 | 0.2 | BLANK | 0 | 0 | 0 | 2 | — | — | 2 | 4 | 3 | 5 | — | — | 3 | 5 |
| | | TEST | 2 | 4 | 7 | 10 | — | — | 8 | 10 | — | — | 7 | 9 | 6 | 7 |

TABLE 7c

SOLVENT = 1,1,1-TRICHLOROETHANE
COLOR INTENSITY AT 2 MINUTES AND 15 MINUTES
COPPER CONCENTRATION (millimolar)

| Guaiac (%) | CHP (%) | Sample Type | .5 | | 1.0 | | 2.0 | | 5.0 | | 10 | | 20 | | 50 | |
|---|---|---|---|---|---|---|---|---|---|---|---|---|---|---|---|---|
| | | | 2 M | 15 M | 2 M | 15 M | 2 M | 15 M | 2 M | 15 M | 2 M | 15 M | 2 M | 15 M | 2 M | 15 M |
| 2.0 | 1.0 | BLANK | 0 | 1 | 0 | 2 | 0 | 2 | 0 | 2 | 0 | 2 | 0 | 2 | 0 | 2 |
| | | TEST | 1 | 3 | 4 | 8 | 8 | 9 | 10 | 10 | 10 | 10 | 10 | 10 | 10 | 10 |
| 0.5 | 1.0 | BLANK | 0 | 1 | 0 | 1 | — | — | 3 | 2 | 3 | 2 | — | — | 4 | 3 |
| | | TEST | 4 | 5 | 7 | 8 | — | — | 7 | 8 | 8 | 8 | — | — | 8 | 8 |
| 0.5 | 0.4 | BLANK | 0 | 0 | 1 | 1 | — | — | 1 | 2 | 2 | 2 | — | — | 2 | 3 |
| | | TEST | 2 | 2 | 6 | 6 | — | — | 6 | 6 | 6 | 6 | — | — | 6 | 6 |

TABLE 7d

SOLVENT = 10% HEXANOL:90% TOLUENE
COLOR INTENSITY AT 2 MINUTES AND 15 MINUTES
COPPER CONCENTRATION (millimolar)

| Guaiac (%) | CHP (%) | Sample Type | .5 | | 1.0 | | 2.0 | | 5.0 | | 10 | | 20 | | 50 | |
|---|---|---|---|---|---|---|---|---|---|---|---|---|---|---|---|---|
| | | | 2 M | 15 M | 2 M | 15 M | 2 M | 15 M | 2 M | 15 M | 2 M | 15 M | 2 M | 15 M | 2 M | 15 M |
| 2.0 | 1.0 | BLANK | 0 | 0 | 0 | 2 | 0 | 4 | 1 | 6 | 1 | 6 | 3 | 8 | 1 | 7 |
| | | TEST | 4 | 5 | 10 | 10 | 10 | 10 | 10 | 10 | 10 | 10 | 10 | 10 | 10 | 10 |
| 0.5 | 1.0 | BLANK | 0 | 0 | 0 | 2 | — | — | 2 | 4 | 1 | 5 | — | — | 3 | 6 |
| | | TEST | 5 | 5 | 8 | 8 | — | — | 8 | 8 | 8 | 8 | — | — | 8 | 8 |
| 0.5 | 0.2 | BLANK | 0 | 0 | 0 | 1 | — | — | 1 | 3 | 1 | 3 | — | — | 2 | 4 |
| | | TEST | 2 | 5 | 7 | 8 | — | — | 7 | 9 | 7 | 9 | — | — | 7 | 9 |

Similar tests were then carried out to determine the optimum metal ion concentration. 100 μl 2.0 mM n-caproic acid (or water in the case of blanks), titrated As anticipated, the acceptable range of component concentrations for each time interval varied with the choice of solvent. Optimum concentrations of various components were determined as follows: (1) where FFA were not present, a color intensity of less than 2 at 2 minutes incubation time was required; and (2) where FFA were present, a color intensity of at least 5 after 10 minutes incubation time was required. Based on these criteria, the optimum concentration ranges for various components are as follows:

TABLE 8

| SOLVENT | GUAIAC (%) | CHP (%) | COPPER (mM) |
|---|---|---|---|
| TOLUENE | 2.0 | 0.4–1.0 | 1.0–50.0 |
| HEXANOL | 0.01–2.0 | 0.02–1.0 | 0.5–10.0 |
| TCE | 0.1–2.0 | 0.2–1.0 | 0.5–50.0 |
| TOL/HEX | 0.1–2.0 | 0.02–1.0 | 0.5–50.0 |

These concentrations ranges, however, are not necessarily suitable for all types of specimens. Various factors such as adsorption to the specimen may influence the final concentration of a given component. The ranges should thus be redefined for each specimen type according to the procedures outlined above.

EXAMPLE 5

Effect of pH

The effect of pH on the present method was evaluated as follows. 100 $\mu$l 50 mM n-caproic acid (at pH shown) and 60 $\mu$l 1 mM cupric sulfate were added to a clean test tube. 100 $\mu$l color developing reagent, containing guaiac, cumene hydroperoxide and solvent at the concentrations indicated in Table 9, were added. The reagent mixture was vortexed for 10 seconds, and color formation was monitored as in the preceding Examples. Results are summarized in Table 9.

TABLE 9

| REAGENT | COLOR INTENSITY SCORES AT 2 MINUTES pH OF AQUEOUS PHASE | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| Toluene |  |  |  |  |  |  |  |  |  |  |  |  |
| 0.5% Guaiac 1.0% CHP | 0 | 0 | 0 | 1 | 5 | 6 | 7 | 7 | 7 | 7 | 6 | 1 |
| Hexanol |  |  |  |  |  |  |  |  |  |  |  |  |
| 0.5% Guaiac .04% CHP | 0 | 0 | 1 | 6 | 8 | 8 | 8 | 8 | 8 | 8 | 7 | 5 |
| TCE |  |  |  |  |  |  |  |  |  |  |  |  |
| 0.5% Guaiac 0.2% CHP | 0 | 0 | 0 | 6 | 8 | 8 | 7 | 7 | 8 | 8 | 6 | 2 |
| TOL/HEX |  |  |  |  |  |  |  |  |  |  |  |  |
| 0.5% Guaiac 0.2% CHP | 0 | 0 | 0 | 5 | 6 | 8 | 8 | 8 | 8 | 8 | 8 | 5 |

As may be concluded from the results, the method is effective over a fairly broad pH range, including over the physiological pH range of 4.5 to 7.4 anticipated with serum, urine, fecal or salivary samples. Only at very low pH (1–3) or at very high pH (>11) was a deterioration of reagent performance observed. Thus, while buffering of the system may be desirable, it is not mandated by pH sensitivity of the method.

EXAMPLE 6

Sensitivity to Caproic Acid

Caproic acid was selected for preliminary sensitivity testing because it is one of the FFA shown to be of diagnostic importance in Ascaris infestations. Monteoliva, M., et al., *Rev. Iberica Parasit.* 41(3): 333–340 (1981); Soprunov, et al., supra. Caproic acid, titrated with sodium hydroxide to a pH of 7.0, at concentrations varying from 0.05 mM to 100 mM (or water in the case of blanks) was admixed with 60 $\mu$l 1 mM cupric sulfate and 100 $\mu$l color developing reagent containing 0.5 wt.% guaiac and 1.0 wt.% cumene hydroperoxide in various solvents as indicated. The reagent mixture was vortexed for 5 seconds, and color formation was monitored after 2 minutes and after 10 minutes. The minimum concentrations of caproate detectable in the various solvent systems are set forth in Table 10:

TABLE 10

| SOLVENT | Minimum Concentration of Caproate Detectable (mM) | |
|---|---|---|
|  | 2 MINUTES | 10 MINUTES |
| TOLUENE | 3.1 | 3.1 |
| HEXANOL | 0.1 | — |
| TCE | 0.8 | 0.4 |
| HEX/TOL | 0.4 | 0.05 |

The data indicate that urinary concentrations of five- and six-carbon FFA which permit diagnosis of Ascaris infestation in humans should be easily detectable with the present test. See, e.g., Soprunova et al., *Angew. Parasitol.* 14: 11–17 (1973) and Kharnakov and Soprunova, *Med. Parazitol. Parazit. Bolezni* 45: 450–452 (1976).

EXAMPLE 7

Further Substrate Specificity Studies

In this example, the specificity of the method for various free fatty acids was evaluated. 50 $\mu$l of sample solution at the concentrations indicated in Tables 11a and 11b, 20 $\mu$l 1 mM cupric sulfate, and 100 $\mu$l color developing reagent containing guaiac and cumene hydroperoxide at the concentrations indicated were added to a microtiter plate well. The plate was agitated for 2 minutes in one experiment (Table 11a) and for 15 minutes in a second experiment (Table 11b). Color formation was monitored as in the previous Examples. Results are set forth in Tables 11a and 11b.

TABLE 11a

| | | 2% G/.5% CHP | | .5% G/.02% CHP | | .5% G/.4% CHP | | .5% G/.2% CHP | |
|---|---|---|---|---|---|---|---|---|---|
| | | COLOR INTENSITY SCORES AT 2 MINUTES | | | | | | | |
| | | TOLUENE | | HEXANOL | | 1,1,1-TCE | | TOL/HEX | |
| Conc. | Compound | Neat | Pure | Neat | Pure | Neat | Pure | Neat | Pure |
| | None* | 0 | 0 | 0 | 0 | 0 | 0 | 0 | 0 |
| | Water | 0 | 1 | 0 | 0 | 2 | 5 | 1 | 1 |
| 0.1 M | 2-OH Butyrate | 0 | 1 | 0 | 0 | 2 | 2 | 0 | 0 |
| .04 M | Acetoacetate | 0 | 2 | 0 | 0 | 1 | 0 | 1 | 0 |
| 0.1 M | Lactate | 0 | 2 | 1 | 0 | 2 | 3 | 2 | 0 |
| " | Pyruvate | 0 | 0 | 0 | 0 | 0 | 0 | 0 | 0 |
| " | Oxaloacetate | 0 | 0 | 0 | 0 | 0 | 0 | 0 | 0 |
| .05 M | 1-Keto glutarate | 0 | 0 | 0 | 0 | 0 | 0 | 0 | 0 |

TABLE 11a-continued

| | | 2% G/.5% CHP | | .5% G/.02% CHP | | .5% G/.4% CHP | | .5% G/.2% CHP | |
|---|---|---|---|---|---|---|---|---|---|
| | | COLOR INTENSITY SCORES AT 2 MINUTES | | | | | | | |
| | | TOLUENE | | HEXANOL | | 1,1,1-TCE | | TOL/HEX | |
| Conc. | Compound | Neat | Pure | Neat | Pure | Neat | Pure | Neat | Pure |
| 0.1 M | Malonate | 0 | 0 | 0 | 0 | 0 | 0 | 0 | 0 |
| " | Malate | 0 | 0 | 0 | 0 | 0 | 0 | 0 | 0 |
| " | Citrate | 0 | 0 | 0 | 0 | 0 | 0 | 0 | 0 |
| " | Tartrate | 0 | 0 | 0 | 0 | 0 | 0 | 0 | 0 |
| " | Fumarate | 0 | 1 | 0 | 0 | 2 | 4 | 1 | 1 |
| " | Maleate | 0 | 1 | 0 | 0 | 2 | 2 | 1 | 0 |
| " | Oxalate | 0 | 0 | 0 | 0 | 0 | 0 | 0 | 0 |
| " | Succinate | 0 | 2 | 0 | 0 | 3 | 4 | 2 | 1 |
| 0.1 M | Glycine | 0 | 0 | 0 | 0 | 0 | 0 | 0 | 0 |
| .01 M | Lysine | 0 | 0 | 0 | 0 | 0 | 0 | 0 | 0 |
| " | Glutamate | 0 | 0 | 0 | 0 | 0 | 0 | 0 | 0 |
| " | Leucine | 0 | 0 | 0 | 0 | 0 | 0 | 0 | 0 |
| 0.1 M | Glucose | 0 | 0 | 0 | 0 | 1 | 1 | 0 | 0 |
| " | Urea | 0 | 2 | 1 | 1 | 4 | 8 | 2 | 2 |
| " | Choline | 0 | 1 | 1 | 1 | 2 | 6 | 2 | 2 |
| .005 M | Uric Acid | 0 | 2 | 0 | 0 | 2 | 4 | 2 | 2 |
| 0.1 M | Ammonium Sulfate | 0 | 0 | 0 | 0 | 0 | 0 | 0 | 0 |
| 0.1 M | NaCl | 0 | 2 | 1 | 0 | 3 | 5 | 2 | 2 |

*Neat = Guaiac used as received from commercial suppliers.
** Pure = Guaiac purified by selective solvent extraction prior to use.

TABLE 11b

| | | 2% G/.5% CHP | | .5% G/.002% CHP | | .5% G/.4% CHP | | .5% G/.2% CHP | |
|---|---|---|---|---|---|---|---|---|---|
| | | COLOR INTENSITY SCORES AT 15 MINUTES | | | | | | | |
| | | TOLUENE | | HEXANOL | | 1,1,1-TCE | | TOL/HEX | |
| Conc. | Compound | Neat | Pure | Neat | Pure | Neat | Pure | Neat | Pure |
| | None* | 0 | 0 | 0 | 0 | 0 | 0 | 0 | 0 |
| | Water | 1 | 2 | 1 | 1 | 4 | 6 | 2 | 4 |
| 0.1 M | OH—Butyrate | 3 | 2 | 1 | 0 | 4 | 3 | 2 | 2 |
| .04 M | Acetoacetate | 4 | 3 | 0 | 0 | 2 | 2 | 2 | 2 |
| 0.1 M | Lactate | 2 | 4 | 1 | 0 | 4 | 5 | 4 | 4 |
| " | Pyruvate | 0 | 0 | 0 | 0 | 0 | 0 | 0 | 0 |
| " | Oxaloacetate | 0 | 0 | 0 | 0 | 0 | 0 | 0 | 0 |
| .05 M | 1-Keto glutarate | 2 | 1 | 0 | 0 | 1 | 2 | 1 | 0 |
| 0.1 M | Malonate | 0 | 0 | 0 | 0 | 0 | 0 | 0 | 0 |
| " | Malate | 0 | 0 | 0 | 0 | 1 | 1 | 0 | 1 |
| " | Citrate | 0 | 0 | 0 | 0 | 0 | 0 | 0 | 0 |
| " | Tartrate | 0 | 1 | 0 | 0 | 0 | 0 | 0 | 0 |
| " | Fumarate | 2 | 2 | 1 | 0 | 4 | 6 | 5 | 4 |
| " | Maleate | 3 | 2 | 1 | 0 | 4 | 5 | 4 | 3 |
| " | Oxalate | 0 | 0 | 0 | 0 | 0 | 0 | 0 | 0 |
| " | Succinate | 2 | 4 | 2 | 1 | 5 | 6 | 6 | 5 |
| 0.1 M | Glycine | 0 | 0 | 0 | 0 | 0 | 0 | 0 | 0 |
| .01 M | Lysine | 0 | 0 | 0 | 0 | 0 | 0 | 0 | 0 |
| " | Glutamate | 0 | 0 | 0 | 0 | 0 | 0 | 0 | 0 |
| " | Leucine | 0 | 0 | 0 | 0 | 0 | 0 | 0 | 0 |
| 0.1 M | Glucose | 0 | 1 | 0 | 0 | 2 | 2 | 1 | 2 |
| " | Urea | 2 | 2 | 4 | 2 | 6 | 8 | 5 | 5 |
| " | Choline | 2 | 1 | 4 | 2 | 4 | 6 | 3 | 4 |
| .005 M | Uric Acid | 2 | 3 | 2 | 1 | 5 | 6 | 4 | 5 |
| 0.1 M | Ammonium Sulfate | 0 | 0 | 0 | 0 | 0 | 0 | 0 | 0 |

As these results demonstrate, it is clearly possible to select a solvent so as to determine concentrations of selected free fatty acids independently of other free fatty acids or metabolites which may be in solution.

EXAMPLE 8

Testing Canine Feces for Free Fatty Acids

In this example, canine feces spiked with 2-methyl valerate was analyzed as follows. A filter paper was spotted with 20 μl of 20 mM cupric sulfate and dried. Approximately 30 μl feces treated 1:1 w/w with either distilled water ("DW") or 40 mM 2-methyl valeric acid ("2MV") was placed on the dried filter paper, and allowed to stand for 10 minutes. The sample was then eluted by placing 30 μl aliquots of solvent (90/10 v/v toluene:hexanol) at the center of the sample on the side opposite feces. A staining reagent (approximately 300 μl) containing 2 wt.% guaiac and 1% cumene hydroperoxide in a 90:10 v/v toluene/hexanol mixture was added and color formation was monitored after a 5-minute incubation period. Results are set forth in Table 12. As may be seen therein, the present method is quite effective in detecting free fatty acids while minimizing the occurrence of "false positives".

TABLE 12

| FECAL SAMPLE NO. | SPIKED COMPOUND | COLOR INTENSITY |
|---|---|---|
| 253 | DW | 0 |
| 254 | 2 MV | 3 |
| 255 | DW | 2 |
| 256 | 2 MV | 5 |
| 257 | DW | 1 |
| 258 | 2 MV | 5 |
| 259 | DW | 0 |
| 260 | 2 MV | 2 |
| 261 | DW | 0 |
| 262 | 2 MV | 0 |
| 263 | DW | 0 |
| 264 | 2 MV | 6 |
| 265 | DW | 0 |
| 266 | 2 MV | 8 |
| 267 | DW | 0 |
| 268 | 2 MV | 6 |
| 269 | DW | 0 |
| 270 | 2 MV | 6 |
| 271 | DW | 0 |
| 272 | 2 MV | 2 |
| 273 | DW | 0 |
| 274 | 2 MV | 6 |
| 275 | DW | 0 |
| 276 | 2 MV | 6 |
| 277 | DW | 0 |
| 278 | 2 MV | 6 |

EXAMPLE 9

Testing Saliva for Free Fatty Acids

Saliva spiked with 2-methyl valeric acid was analyzed substantially according to the method of the preceding example. Filter paper was spotted with 20 μl of 20 mM cupric sulfate and dried. 30 μl saliva spiked 1:1 v/v with either distilled water or 20 mM 2-methyl valeric acid was added. The sample was allowed to stand 10 minutes, after which time the sample was eluted by addition of 30 μl aliquots of solvent (90/10 v/v toluene/hexanol) at the center of the sample on the same side as the specimen. Color developing reagent (2 wt.% guaiac and 1 wt.% cumene hydroperoxide in 90:10 v/v toluene/hexanol) was added, and color formation was observed after a 5-minute incubation period. Results are tabulated in Table 13. As in the preceding Example, the method was found to give a positive test.

TABLE 13

| SALIVA SAMPLE NO. | SPIKED COMPOUND | COLOR INTENSITY |
|---|---|---|
| 1 | DW | 0 |
|   | 2 MV | 8 |
| 2 | DW | 0 |
|   | 2 MV | 3 |
| 3 | DW | 0 |
|   | 2 MV | 7 |
| 4 | DW | 0 |
|   | 2 MV | 6 |
| Control (No Saliva) | DW | 0 |
|   | 2 MV | 6 |

EXAMPLE 10

Detection of Alternative Carboxylic Acids 100 mM aqueous solutions of various carboxylic acids (see Table 14) were titrated to pH 7 with sodium hydroxide. Filter paper was spotted with 20 μl aliquots of 5, 10, 20 and 50 mM aqueous cupric sulfate solutions and dried. Twenty μl of each acid solution were added to a series of cupric sulfate spots and eluted while wet with 90/10 v/v toluene/hexanol. Migration of the acid/copper complexes was detected with color developing reagent (2 wt.% guaiac and 1 wt.% cumene hydroperoxide in 90:10 v/v toluene/hexanol).

TABLE 14

Color Intensity of Eluted Complex

| Acid | Copper Concentration, mM: | | | |
|---|---|---|---|---|
|  | 5 | 10 | 20 | 50 |
| 2-Methyl Valeric | 7 | 8 | 8 | 8 |
| Benzoic | 4 | 5 | 5 | 6 |
| Salicylic | 1 | 4 | 5 | 6 |
| Acetyl-salicylic | 4 | 5 | 7 | 8 |
| Sulfanilic (a sulfonic acid) | 0 | 0 | 1 | 2 |
| Isonicotinic | 0 | 1 | 1 | 1 |
| L-Pyroglutamic | 0 | 0 | 1 | 1 |
| N—acetyl-L-Leucine | 3 | 5 | 7 | 8 |
| (Distilled Water) | 0 | 0 | 0 | 0 |

At the lower concentrations of copper sulfate typically employed for the detection of volatile fatty acids, the test system was most sensitive to 2-MV. Varying degrees of sensitivity were observed for the other acids. These data, along with those presented previously, indicate that the test may be used to detect selected carboxylic acids other than the volatile fatty acids.

We claim:

1. A method of analyzing a specimen to determine if carboxylic acids are present therein, comprising:
   (a) providing a solid support on which a serum, fecal, urine or salivary specimen has been smeared;
   (b) contacting the specimen with a developing system comprising (i) a metal salt reactive with carboxylic acids so that when the specimen contains carboxylic acids, metal-carboxylic acid complexes will be formed, wherein said metal salt is initially present on said solid support and is selected from the group consisting of iron, silver and copper salts; (ii) an organic phase containing a solvent in which selected metal-carboxylic acid complexes are substantially soluble and in which the metal salt is substantially insoluble; (iii) a chromogen; and (iv) an oxidant capable of oxidizing the chromogen to a colored compound in the presence of metal-carboxylic acid complexes; and
   (c) detecting the presence of any such metal-carboxylic acid complexes formed by monitoring the catalytic activity of such complexes.

2. A method of analyzing a specimen to determine if carboxylic acids are present therein, comprising:
   (a) providing a solid support on which a serum, fecal, urine or salivary specimen has been smeared;
   (b) contacting the specimen with a developing system comprising (i) a metal salt reactive with carboxylic acids so that when the specimen contains carboxylic acids, metal-carboxylic acid complexes will be formed, wherein said metal salt is selected from the group consisting of iron, silver and copper salts; (ii) an organic phase containing a solvent in which selected metal-carboxylic acid complexes are substantially soluble and in which the metal salt is substantially insoluble; (iii) a chromogen initially present on the solid support; and (iv) an oxidant capable of oxidizing the chromogen to a colored compound in the presence of metal-carboxylic acid complexes; and
   (c) detecting the presence of any such metal-carboxylic acid complexes formed by monitoring the catalytic activity of such complexes.

3. A method of analyzing a specimen to determine if carboxylic acids are present therein, comprising:
  (a) providing a solid support on which a serum, fecal, urine or salivary specimen has been smeared;
  (b) contacting the specimen with a developing system comprising (i) a metal salt reactive with carboxylic acids so that when the specimen contains carboxylic acids, metal-carboxylic acid complexes will be formed; (ii) an organic phase containing a solvent in which selected metal-carboxylic acid complexes are substantially soluble and in which the metal salt is substantially insoluble; (iii) a chromogen; and (iv) an oxidant capable of oxidizing the chromogen to a colored compound in the presence of metal-carboxylic acid complexes; and
  (c) detecting the presence of any such metal-carboxylic acid complexes formed by monitoring the catalytic activity of such complexes.

4. The method of claim 3, wherein the metal salt is selected from the group consisting of iron, silver and copper salts.

5. The method of claim 4, wherein the developing system further comprises an aqueous phase containing the metal salt.

6. The method of claim 4, wherein the chromogen is initially present in the organic phase.

7. The method of claim 4, wherein the carboxylic acids are indicative of intestinal helminth infestation.

8. The method of of claim 4, wherein the metal salt is a copper salt, the chromogen is guaiac and the oxidant is cumene hydroperoxide.

9. A method of analyzing a specimen to determine if carboxylic acids are present therein, comprising:
  (a) contacting a specimen with a metal salt reactive with carboxylic acids so that when the specimen contains carboxylic acids, metal-carboxylic acid complexes will be formed; and
  (b) detecting the presence of any such metal-carboxylic acid complexes formed by monitoring the catalytic activity of such complexes.

10. The method of claim 9, wherein the metal salt is present on a solid support.

11. The method of claim 9, wherein the metal salt is present in a developing system comprising: (a) an organic phase containing a substantially water-immiscible solvent; (b) a chromogen; and (c) an oxidant capable of oxidizing the chromogen to a colored compound.

12. The method of claim 11 wherein the developing system further comprises (d) an aqueous phase wherein the metal salt is substantially soluble.

13. The method of claim 12, wherein the solvent is selected which has the property to isolate in the organic phase metal-fatty acid complexes formed from five-carbon fatty acids, six-carbon fatty acids, succinic acid or mixtures thereof.

14. The method of claim 13, wherein the solvent is selected from the group consisting of toluene, 1,1,1-trichloroethane, benzyl alcohol, isopropyl benzyl alcohol, dichloromethane, ethyl acetate, octyl acetate, cumene, benzyl benzoate, hexanol and mixtures thereof.

15. The method of claim 9, wherein the metal salt is selected from the group consisting of iron, silver and copper salts.

16. The method of claim 15, wherein the contacting is effected at a pH of between about 4 and about 11.

17. The method of claim 15, wherein the carboxylic acids detected are free fatty acids indicative of intestinal helminth infestation.

18. The method of claim 17, wherein the specimen comprises a serum, fecal, urine or salivary sample.

19. The method of claim 15, wherein the concentration of metal salt in the developing system is between about 0.5 mM and about 50 mM.

20. The method of claim 19, wherein the concentration is between about 0.1 mM and about 10 mM.

21. The method of claim 15, wherein the catalytic activity of the metal-carboxylic acid complexes is detected colorimetrically.

22. The method of claim 21, wherein the metal-carboxylic acid complexes are detected by their activity in catalyzing the oxidation of a chromogen.

23. The method of claim 22, wherein the metal-carboxylic acid complexes catalyze oxidation of a chromogen by an oxidant from a colorless, reduced state to a colored, oxidized state.

24. The method of claim 23, wherein the metal salt is a copper salt, and the oxidant is selected from the group consisting of hydrogen peroxide, cumene hydroperoxide, t-butyl hydroperoxide, diisopropylbenzene hydroperoxide, 2,5-dimethylhexane hydroperoxide and mixtures thereof.

25. The method of claim 24, wherein the oxidant is cumene hydroperoxide.

26. The method of claim 23, wherein the metal salt is a copper salt, and the chromogen is selected from the group consisting of guaiac, 4-chloro-1-naphthol, ortho-phenylenediamine, tetramethylbenzidine, leucomalachite green, 2,2-azinobis(3-methoxy diphenylamine), ortho-dianisidine, 5-amino salicylic acid, and mixtures thereof.

27. The method of claim 26, wherein the chromogen is guaiac.

28. The method of claim 27, wherein the oxidant is cumene hydroperoxide.

* * * * *

UNITED STATES PATENT AND TRADEMARK OFFICE
CERTIFICATE OF CORRECTION

PATENT NO. : 4,777,143

DATED : 11 October 1988

INVENTOR(S) : Neil H. Price and Paul J. Lawrence

It is certified that error appears in the above-identified patent and that said Letters Patent is hereby corrected as shown below:

In the Figure:

In the cover page and in the figure, delete "fumarata" and substitute therefor -- FUMARATE --.

In the Specification:

At column 5, line 17, kindly replace "(3-methoxy diphenylamine)" with --3-amino-3-methoxydiphenylamine--.

In Table 2, correct "GUALAC" to read "GUAIAC".

In Table 2, please delete the results adjacent the second "benzyl alcohol", i.e., at line 13 of the table, beneath "4-isopropyl-".

In Table 2, please add the following results next to the solvent "benzyl alcohol" at line 11 of the table, beneath "ethylene glycol":

Under "Water Miscibility", please add -- - --.

Under "GUAIAC Solubility", kindly add --+++--.

Under "$H_2O$", please add --4--.

Under "NaCl", kindly add --7--.

Under "Me-C-4", please add --10--.

Under "C-5", kindly add --10--.

UNITED STATES PATENT AND TRADEMARK OFFICE
CERTIFICATE OF CORRECTION

PATENT NO. : 4,777,143

DATED : 11 October 1988

INVENTOR(S) : Neil H. Price and Paul J. Lawrence

It is certified that error appears in the above-identified patent and that said Letters Patent is hereby corrected as shown below:

Under "Me-C-5", kindly add --10--.

Under "Suc.", please add --7--.

Under "Lac", please add --4--.

Under "Cit.", kindly add --0--.

In Claim 26, please add, after "2,2-azinobis", --(3-ethylbenzothiazoline-6-sulfonic acid) and--.

Signed and Sealed this

Twenty-fourth Day of October, 1989

Attest:

DONALD J. QUIGG

Attesting Officer

Commissioner of Patents and Trademarks